United States Patent
Grob

Patent Number: 5,562,660
Date of Patent: Oct. 8, 1996

[54] APPARATUS FOR STIFFENING AND/OR CORRECTING THE VERTEBRAL COLUMN

[75] Inventor: Dieter Grob, Zürich, Switzerland

[73] Assignee: Plus Endoprothetik AG, Switzerland

[21] Appl. No.: 318,894

[22] PCT Filed: Feb. 2, 1994

[86] PCT No.: PCT/EP94/00302

§ 371 Date: Oct. 7, 1994

§ 102(e) Date: Oct. 7, 1994

[87] PCT Pub. No.: WO94/17745

PCT Pub. Date: Aug. 18, 1994

[30] Foreign Application Priority Data

Feb. 9, 1993 [DE] Germany ............... 43 03 770.4

[51] Int. Cl.⁶ ............... A61B 17/70; A61B 17/86
[52] U.S. Cl. ............... 606/61; 606/73
[58] Field of Search ............... 606/61, 60, 72, 606/73, 86, 105, 57, 58

[56] References Cited

U.S. PATENT DOCUMENTS

| | | | |
|---|---|---|---|
| 3,997,138 | 12/1976 | Crock et al. | 606/61 |
| 4,658,609 | 4/1987 | Ulrich et al. | 129/92 |
| 4,658,809 | 4/1987 | Ulrich et al. | 606/61 |
| 4,987,892 | 1/1991 | Krag et al. | 606/61 |
| 5,010,879 | 4/1991 | Moriya et al. | 128/69 |
| 5,176,679 | 1/1993 | Lin | 128/92 |
| 5,196,013 | 3/1993 | Harms et al. | 606/61 |
| 5,304,179 | 4/1994 | Wagner | 606/61 |
| 5,382,248 | 1/1995 | Jacobson et al. | 606/61 |
| 5,425,732 | 6/1995 | Ulrich | 606/61 |

FOREIGN PATENT DOCUMENTS

| | | |
|---|---|---|
| 0328883 | 1/1989 | European Pat. Off. . |
| 0383992 | 6/1989 | European Pat. Off. . |
| 0452792 | 4/1991 | European Pat. Off. . |
| 3306657 | 2/1983 | Germany . |
| 2252732 | 10/1991 | United Kingdom . |
| 2254394 | 10/1992 | United Kingdom . |
| 8707134 | 12/1987 | WIPO . |

*Primary Examiner*—Michael H. Thaler
*Assistant Examiner*—Scott B. Markow
*Attorney, Agent, or Firm*—Andrus, Sceales, Starke & Sawall

[57] ABSTRACT

An apparatus for stiffening and/or correcting part of the vertebral column consisting of at least two vertebral is disclosed. The apparatus includes at least two screw-shaped retaining devices (12), each of which is fixed to one of the vertebrae in the affected part of the vertebral column. A compression or distraction rod (32) connects the retaining devices (12) to one another. The compression or distraction rod (32) includes a rod-shaped connecting element (20) connected to the retaining devices (12). The rod-shaped connecting element has at least one distance element (34) and arranged and mounted on such element between the two adjacent retaining devices (12) so as to maintain the distance between these two retaining devices (12). The connecting element (20) at one end (36) has a screw thread (38) and at the other end (42) has either a screw thread (44) or, where appropriate, a flange-like portion (50) to fix in position or brace the retaining devices (12) and distance element (34, 34', 34", 34''', 34"").

20 Claims, 4 Drawing Sheets

APPARATUS FOR STIFFENING AND/OR CORRECTING THE VERTEBRAL COLUMN

BACKGROUND OF THE PRESENT INVENTION

The invention relates to an apparatus for stiffening and/or correcting a part of the vertebral column consisting of at least two vertebrae, according to the precharacterizing clause in claim 1.

Apparatuses of this kind for stiffening and/or correcting a part of the vertebral column consisting of at least two vertebrae are known in the state of the art. Such an apparatus comprises at least two screw-like retaining devices, which can be appropriately fixed to one of the vertebrae in the affected part of the vertebral column. The retaining devices are provided to receive and hold in place a compression or distraction rod that connects the retaining devices to one another. This arrangement allows stiffening or so-called spondylodesis of individual parts of the vertebral column and/or correction in cases of spinal curvature (scoliosis, kyphosis), misalignment (rotation), injury (trauma), neoplasms (tumor) and in particular abrasion or degenerative spinal disease, according to the principle of osteosynthesis that is as rigid as possible and hence extremely stable mechanically.

The retaining devices in these apparatuses as a rule take the form of screws or so-called pedicle screws as well as hooks known per se, which can be connected to one another by way of a mechanically stable compression or distraction rod. An aspect of these apparatuses that has proved decidedly disadvantageous is the structure of the part that connects each retaining device to the compression or distraction rod. On the one hand, the height of the connecting part of these apparatuses is usually relatively great, which severely delays healing after surgery. On the other hand, various mechanical problems are encountered in assembling the apparatus, which both prevent permanent fixation and make it impossible to carry out corrective repositioning later on. Another disadvantage of these apparatuses is that they offer little or no opportunity to vary the length of the fixed region. Instead, different apparatuses must be used, some exclusively for short lengths and others exclusively for great lengths, and because they are not interchangeable their versatility in use is severely restricted. Furthermore, only a very limited force can be applied to these apparatuses, not least because of their construction, in order to correct misalignments of the affected part of the spine. Finally, all these apparatuses are also relatively expensive.

SUMMARY OF THE PRESENT INVENTION

The invention is thus directed to the disclosing an apparatus of this generic kind for the stiffening and/or correction of a part of the vertebral column consisting of at least two vertebrae, which eliminates all the disadvantages of apparatuses known in the state of the art: in particular, the apparatus of this invention is very small in construction, enables permanent, non-self-releasing fixation and can be repositioned after the initial placement, is versatile in use and is able to sustain large forces.

This problem is solved by the characterizing features in claim 1.

By the construction in accordance with the invention, such that the compression or distraction rod comprises a rod-shaped connecting element that can be received by the retaining devices and at least one distance element, each of which is displaceably receivable by the rod-shaped connecting element and positioned between two adjacent retaining devices so as to determine the distance between these retaining devices, the connecting element being provided at one end with a screw thread and at the other end likewise with a screw thread or where appropriate with a flange-like thickening or the like to fix or brace the retaining devices and distance element, various advantages are achieved simultaneously. Not only is the structure compact, it also enables permanent fixation of the apparatus in accordance with the invention after the surgical operation, so that the retaining devices do not release themselves from the connecting element with the at least one distance element that comprise the compression or distraction rod as a whole. Furthermore, the apparatus in accordance with the invention is extremely easy to manipulate during the operation, and at the same time, after its initial placement it can be repositioned by the surgeon with no difficulty. In addition, the apparatus in accordance with the invention can be used in many different situations, because its length is arbitrarily adjustable by way of a rod-shaped connecting element of varying length and one or more distance elements of different lengths, so that it can be adapted to the particular spatial and body-specific peculiarities of each individual patient. Finally, with the apparatus in accordance with the invention a very large force can be exerted because of an immediate postoperative stability at and between the vertebrae of the affected part of the vertebral column, so that positional adjustment or correction of a misalignment can be achieved by the apparatus of the invention itself. As an alternative to the construction with screw-like retaining devices, it is equally possible to employ hook-shaped retaining devices such as are known in the state of the art.

Other forms of the invention are disclosed described in claims 2 to 19.

According to one feature within the scope of the invention the faces of the two ends of the at least one distance element coincide with the plane perpendicular to the long axis of the distance element. In this embodiment, therefore, the distance element consists of a hollow cylinder or the like with both ends straight, so that the retaining devices that abut the distance element extend exactly perpendicular to the distance element itself and to the rod-shaped connecting element of the compression or distraction rod.

In an alternative design, one of the faces of the two ends of the at least one distance element lies in the plane perpendicular to the long axis of the distance element and one of the faces of the two ends of the at least one distance element lies in a plane other than the plane perpendicular to the long axis of the distance element. In this embodiment of the distance element, therefore, the hollow cylinder or the like is cut straight at one end and slanted at one end, so that one of the retaining devices that abut the distance element extends exactly perpendicular to and the other is slanted at an angle to the distance element itself and to the rod-shaped connecting element of the compression or distraction rod. As a result, for example, slight inaccuracies in inserting one of the two retaining devices into the vertebra, due to an imprecisely centered bore or the like, can later be corrected and compensated. Correspondingly, it is possible to adjust the vertebrae in the part of the vertebral column to be stiffened or corrected exactly with respect to one another during the operation by arranging several distance elements with differently shaped ends on the rod-shaped connecting element of the compression or distraction rod, in any desired combination.

Accordingly, it is also provided in accordance with the invention that the faces of both ends of the at least one distance element lie in a plane other than the plane perpendicular to the long axis of the distance element. In this embodiment, therefore, the distance element is a hollow cylinder or the like cut at an angle at both ends, so that each of the retaining devices abutting the distance element is slanted at a corresponding angle to the distance element itself and to the rod-shaped connecting element of the compression or distraction rod. Thus the apparatus in accordance with the invention can be adapted to all kinds of anatomical peculiarities of the patient.

The distance element is advantageously constructed in different lengths, which can additionally increase the versatility of the apparatus in accordance with the invention in dependence on the length of the rod-shaped connecting element.

Of special interest for high rotational stability of the at least one distance element with respect to the two adjacent retaining devices, or of the distance elements with respect to one another, are other special characteristics of the elements. According to these, the end faces of each distance element are roughened to provide rotationally stable contact with the retaining device or devices and/or with the adjacent distance element or elements. In particular, to achieve rotationally stable contact the end faces of each distance element are provided with approximately radially oriented grooves, notches or the like and with corresponding projections. It is also entirely conceivable in this regard that the retaining devices, in those regions that can be brought into contact with the faces of the distance element or elements, are similarly roughened or provided with such radially oriented grooves, notches, etc. as well as projections, etc.

In order to further improve the manipulability of the apparatus in accordance with the invention, the at least one distance element has at its outer circumference a key surface, by means of which the distance element can be rotated about its long axis during installation by means of a tool, in particular a wrench. This also offers the advantage that the apparatus can be adjusted or its position precisely corrected, as necessitated by the deformation or misalignment of the vertebrae in the affected part of the vertebral column. Quite apart from this, given that at least the one distance element has at least one end cut at an angle with respect to its long axis, the bracing force to be exerted, i.e. the clamping force, can in addition be easily, rapidly and precisely adjusted during the surgical operation.

Further features of crucial significance for the versatility of the apparatus in accordance with the invention are also disclosed. That is, there can be provided an additional rod-shaped connecting element, also receivable by retaining devices, that can be arranged at least partially and substantially parallel to the one rod-shaped connecting element receivable by retaining devices and fixed in position with respect to the latter. As a result of such an additional means of fixing the compression or distraction rod, the stability of the apparatus in accordance with the invention can be further increased, so that the affected part of the vertebral column is more stably anchored.

One way to implement such features include having at least one distance element and substantially in parallel therewith having an additional distance element inseparably attached to the first element, in particular by welding. The additional, substantially parallel distance element serves simultaneously to join or connect two apparatuses to be installed in accordance with the invention, whereby it allows arbitrary lengthening or extension of the one or the other previously installed apparatus, and to displace the entire compression or distraction rod in order to adjust the latter to the particular anatomical peculiarities of the patient.

As an alternative to the above embodiment of the apparatus the two rod-shaped connecting elements, receivable by the retaining devices, are connected with one another by way of holder elements that preferably include two or more apertures or the like within which the two rod-shaped connecting elements can be seated with no play.

The retaining devices may also advantageously each comprise a threaded screw shaft to be screwed into the vertebra and a screw head to receive and fix the rod-shaped connecting element. In addition to enabling permanent fixation of the apparatus in accordance with the invention for the purpose of stiffening and/or correcting a part of the vertebral column comprising at least two vertebrae, this embodiment is especially small in size while simultaneously allowing the transfer of large forces, so as to ensure that great force can be applied.

As an additional advantageous means of preventing the whole apparatus from coming loose of its own accord, it is provided in accordance with the invention that the screw head of the screw-shaped retaining device includes a bore, preferably a central bore, into or through which the rod-shaped connecting element can be inserted, substantially without play, by displacing the latter in the direction of its long axis.

In a design alternative to the immediately above, the screw head of the screw-shaped retaining device is provided with a longitudinal slot, into which the rod-shaped connecting element can be set approximately without play by a sideways displacement. This measure enormously simplifies the manipulation of the apparatus in accordance with the invention as it is installed or removed during the surgical operation.

To improve the correction possibilities still further, it is also within the scope of the invention that the screw head and the screw shaft of the screw-shaped retaining device are connected to one another by a transverse bridge and/or by a longitudinal bridge.

In a preferred embodiment of the invention the retaining device and/or the rod-shaped connecting element and/or the nuts that cooperate with the connecting element are made of metal, in particular a metal alloy. A suitable metal or metal alloy, for example, is titanium or an alloy thereof. Such a material increases the compatibility of the apparatus in accordance with the invention even during surgery as well as in the subsequent healing phase, and hence enhances the quality of the operation. In this regard, of course, the material of which the rod-shaped connecting element is made should be such that the rod-shaped connecting element is both highly resistant to bending and nevertheless capable of being bent to at least a certain degree, to permit fine adjustment and/or precise positional correction of the apparatus in accordance with the invention during the operation.

To increase the compatibility of the apparatus, the distance element(s) also consist of metal, in particular titanium or an alloy thereof.

Finally, the distance element(s) can alternatively or cumulatively also be made of a somewhat elastic/flexible material such as polyethylene. The apparatus in accordance with the invention can then stiffen a part of the vertebral column up to a predetermined degree, which depends on the flexibility and elasticity of the material and of the arrangement as a whole.

BRIEF DESCRIPTION OF THE DRAWINGS

Additional characteristics, advantages and details of the invention will become apparent in the following description of some preferred embodiments of the invention, with reference to the drawings, wherein.

DESCRIPTION OF THE ILLUSTRATED EMBODIMENT

Figure 1:
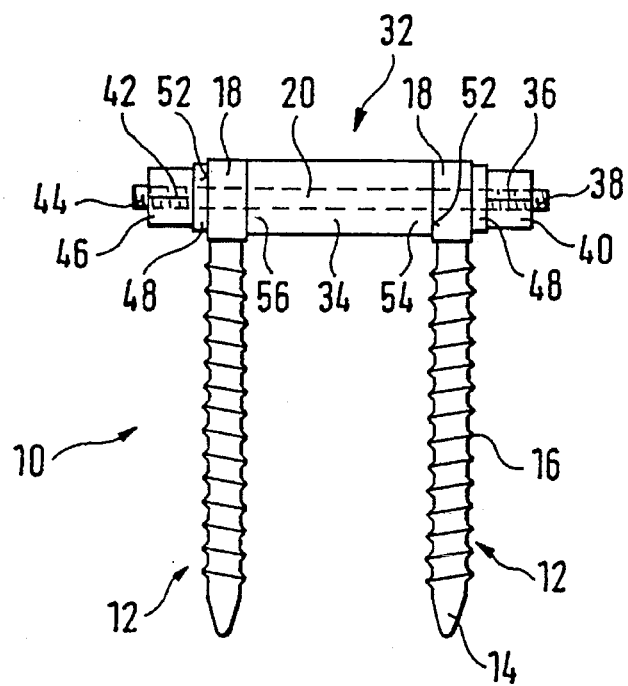
FIG. 1 is a side view of an embodiment of an apparatus constructed in accordance with the invention.
Figure 2:
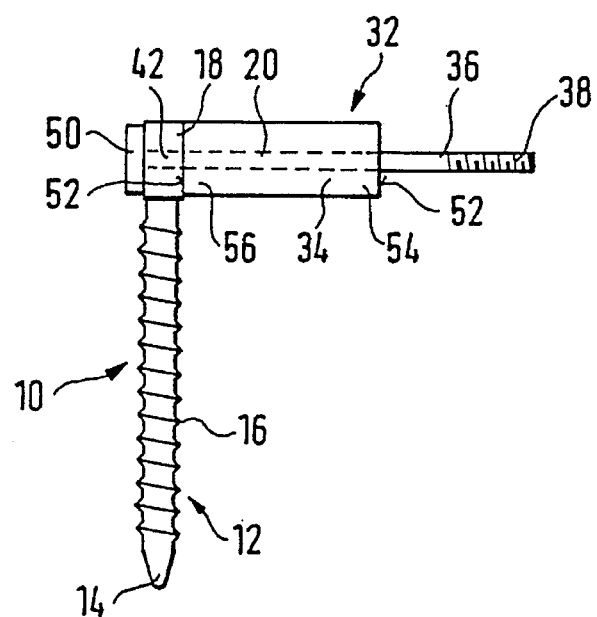
FIG. 2 is a side view of another embodiment of an apparatus constructed in accordance with the invention, which omits the second retaining device with washer and nut.
Figure 4A:
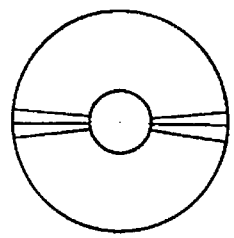
FIG. 4 is a side view of still another embodiment of an apparatus constructed in accordance with the invention.
Figure 3:
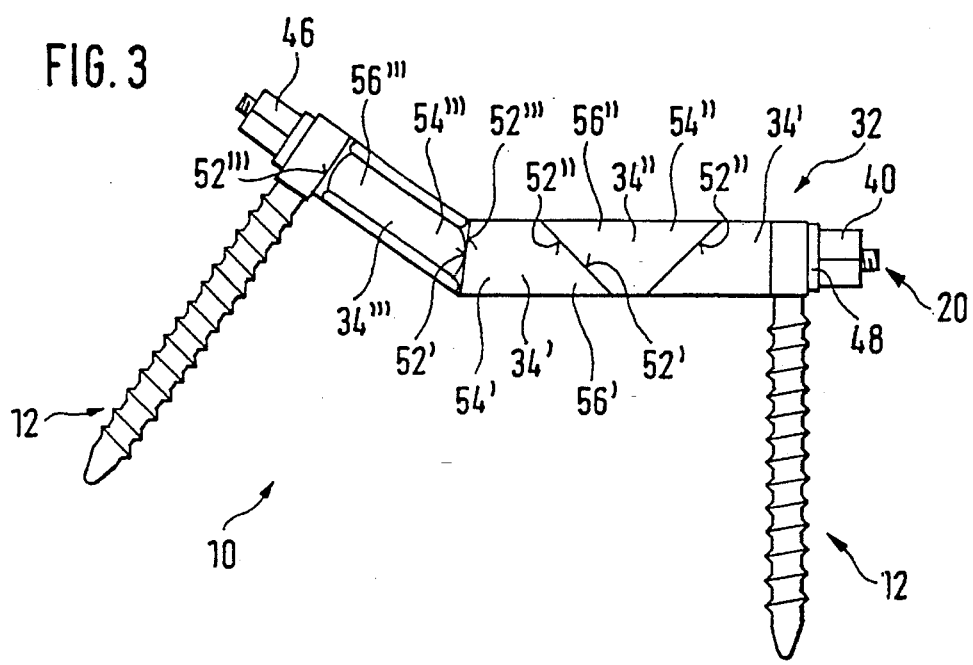
FIG. 3 is a side view of another embodiment of an apparatus constructed in accordance with the invention.
Figure 4:
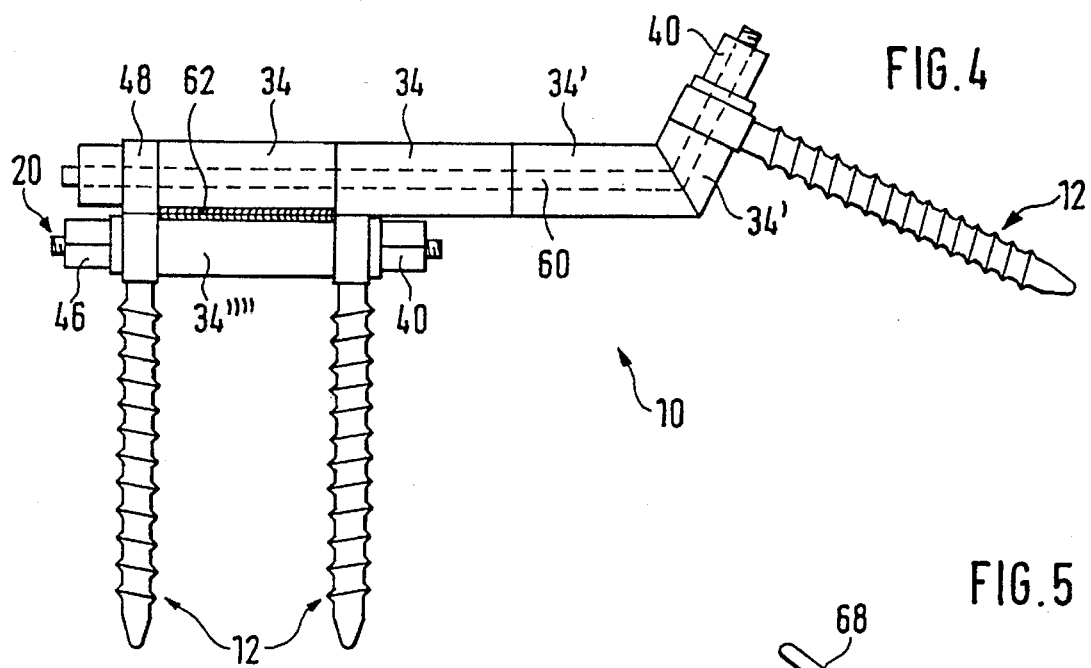

FIG. 1 shows a first embodiment of an apparatus 10 for the stiffening and/or correction of a part of the vertebral column consisting of at least two vertebrae (not illustrated). The embodiment of the apparatus 10 according to FIG. 1, like the other embodiments of the apparatus 10 according to FIGS. 2 to 4, is suitable for dorsal implantation in the lumbar, thoracic and lower cervical regions of the vertebral column and for ventral implantation in the lumbar and middle to lower thoracic regions. For both dorsal and ventral application of the apparatus 10 the fusion can either occur in situ, with or without additional intervention such as decompression, débridement etc., or be accompanied by correction of positional defects such as scoliosis, kyphosis, rotation etc., in which case the etiology of the deformity—trauma, osseous defects, neurogenic, musculogenic or congenital deformities and so on—is irrelevant.

The first embodiment of the apparatus 10, in FIG. 1, comprises two screw-shaped retaining devices 12, each of which can be fixed to one of the vertebrae of the affected part of the vertebral column. In particular, such a retaining device 12 is screwed into the pedicle, i.e. into the vertebral arch between spinous process, transverse process and the corresponding superior articular process.

The screw-shaped retaining devices 12 each comprise a screw shaft 14 with a screw thread 16 by which to be screwed into the vertebra of the affected part of the vertebral column. The screw-shaped retaining devices 12 each further comprise a screw head 18 to receive and fix a rod-shaped connecting element 20.

Figure 6:
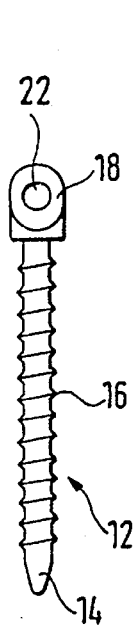
FIGS. 6 to 9 are front and back views of several embodiments of screw-shaped retaining devices constructed in accordance with the invention.
Figure 7:
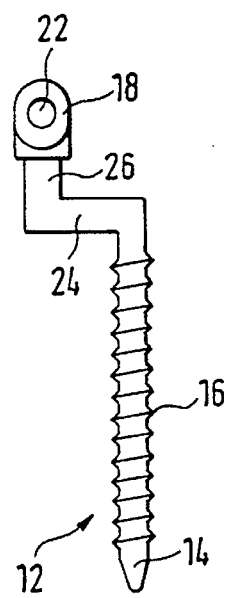

In order to receive the rod-shaped connecting element 20 approximately without play, the screw head 18 of the screw-shaped retaining device 12—as shown in FIGS. 6 and 7—is provided with a bore, preferably a central bore 22. The screw-shaped retaining device 12 can thus be slipped or otherwise placed onto the rod-shaped connecting element 20 by a sliding movement in the direction of the long axis of the connecting element 20 or of the central bore 22 provided in the screw head 18.

The embodiment of the screw-shaped retaining device 12 according to FIG. 7 differs from that according to FIG. 6 merely in that the screw head 20 with the central bore 22 is additionally connected to the screw shaft 14 of the screw-shaped retaining device 12 by way of a cross bridge 24 and a longitudinal bridge 26. This arrangement achieves an additional degree of freedom in the manipulation of the apparatus 10 in accordance with the invention, with the result that the connecting element 20 can be precisely adjusted and if necessary, positional correction can be carried out after the initial placement. The additional degree of freedom refers to the different orientation of the rod relative to the screw as provided by the two devices. Thus, the screw in FIG. 6 provides direct rotation of the screw shaft on the rod axis. The screw of FIG. 7 provides rotational positioning of the rod in the screw head on a circle about the rod axis. Thus the two units together provide additional freedom of movement for positioning in use.

Figure 8:
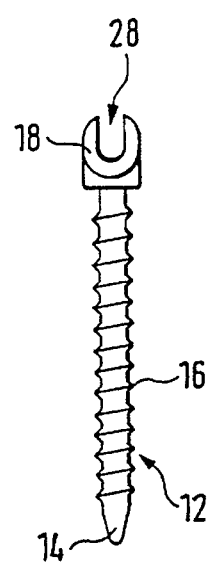
Figure 9:
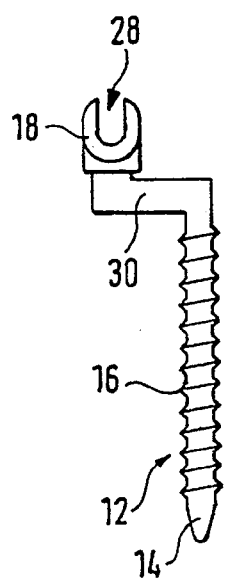

So that the rod-shaped connecting element 20 can be received substantially without play, the screw head 18 of the screw-shaped retaining device 12 is alternatively—as shown in FIGS. 8 and 9—provided with a longitudinal slot, preferably a median longitudinal slot 28, or similar slot-shaped recess. The screw-shaped retaining device 12 can thus be brought onto the rod-shaped connecting element 20 by a sideways placement movement or the like, as a result of which the screw-shaped retaining device 12 becomes considerably easier for the surgeon to manipulate during the operation.

The embodiment of the screw-shaped retaining device 12 according to FIG. 9 differs from that according to FIG. 8 only in that the screw head 18 is not directly continuous with the screw shaft 14 of the screw-shaped retaining device 12, but rather is connected to the screw shaft 14 by way of a cross bridge 30. It is also conceivable in this regard for the screw head 18 and the screw shaft 14 to be connected to one another by way of a longitudinal bridge (not illustrated) extending in the long direction of the screw-shaped retaining device 12, instead of the cross bridge 30. The resulting additional degree of freedom increases many-fold the precision during adjustment and, where necessary, later positional correction by the apparatus 10 in accordance with the invention for the stiffening and/or correction of the part of the vertebral column. Furthermore, the apparatus 10 in accordance with the invention can be flexibly adapted to the particular anatomical features of each individual patient, so that the entire apparatus 10 is extremely versatile in application.

The two retaining devices 12 according to FIG. 1 are provided to receive and fix a compression or distraction rod 32 that connects the two retaining devices 12 to one another. The compression or distraction rod 32 comprises on the one hand the rod-shaped connecting element 20 receivable by the retaining devices 12, and on the other hand at least one, in the illustration only one, distance element 34. The distance element 34 can be received displaceably and substantially without play by the rod-shaped connecting element 20 corresponding to the retaining devices 12. Furthermore, the distance element 34 is disposed between two adjacent retaining devices 12, in order to maintain the distance between these two retaining devices 12.

As is clearly evident in FIGS. 1 and 2, the connecting element 20 is provided at one end 36 with a screw thread 38, which cooperates with a nut 40 as shown in FIG. 1. At the other end 42 the connecting element 20 according to FIG. 1 is likewise equipped with a screw thread 44 for a nut 46. At each of the two ends, between the nut 40 or 46 and the neighboring retaining device 12 there is disposed on the connecting element 20 a plain washer 48, a locking ring or the like. Consequently when the two nuts 40, 46 are tightened, the two retaining devices 12 and the distance element 34 disposed between the two retaining devices 12 are fixed to one another or even braced against one another.

The further embodiment of the apparatus 10 in accordance with the invention for the stiffening and/or correction of part of the vertebral column according to FIG. 2 is distinguished from that in FIG. 1 merely in that the connecting element 20 is provided at the one end 36 with a screw thread 38 and a nut 40 (not shown), but at the other end 42 with a flange-like thickening 50 or the like instead of the screw thread 44 and the nut 46. Here, therefore, the two retaining devices 12 and the distance element 34 inserted between the two retaining devices 12, all of which are disposed on the connecting element 20, are fixed to one another or mutually braced between the flange-like thickening and the one (not illustrated) nut 40 merely by tightening said nut. As an additional means of reliably preventing the apparatus from loosening of its own accord, for example, a plain washer, locking ring or the like not illustrated in FIG. 2 can be provided. All the remaining components that correspond to those of the embodiment of the apparatus 10 according to FIG. 1 are indicated by the same reference numerals.

As is further evident in FIGS. 1 and 2, the faces 52 of the two ends 54, 56 of the at least one, here the only, distance element 34 lie in the plane perpendicular to the long axis of the distance element 34, in the drawing also perpendicular to the plane of the page. The distance element 34 according to FIGS. 1 and 2 thus has the form of a hollow cylinder cut straight across at both ends.

The embodiment of the apparatus 10 in accordance with the invention for the stiffening and/or correction of part of the vertebral column shown in FIG. 3 differs from that of FIG. 1 only in the special form of the individual distance elements 34', 34" and 34'". All the remaining components that correspond to those of the embodiment of the apparatus 10 according to FIG. 1 are indicated by the same reference numerals.

As shown in FIG. 3, in the case of the two distance elements 34' one of the faces 52' of the two ends 54', 56', here the end 54', lies in the plane perpendicular to the long axis of the distance element 34' and to the plane of the page. Furthermore, in the case of the two distance elements 34' in FIG. 3 one of the faces 52' of the two ends 54', 56', here the end 56', lies in a plane other than that perpendicular to the long axis of the distance element 34' and hence also to the plane of the page. The distance element 34' is thus quasi a hollow cylinder with one end cut straight across and the other slanted.

Another distance element 34" according to FIG. 3 has faces 52" at both ends 54", 56" that lie in a plane different from that perpendicular to the long axis of the distance element 34" and hence also to the plane of the page. The distance element 34" thus has the form of a hollow cylinder or the like with both ends cut at an angle.

Finally, FIG. 3 also shows a distance element 34'", the outer circumference of which is provided with a key surface or the like, to allow the distance element 34'" to be rotated about its long axis by means of a tool, in particular a wrench. One of the faces 52'" of the two ends 54'", 56'" of the distance element 34'" lies in the plane perpendicular to the long axis of the distance element 34'" and one of the faces 52'" of the two ends 54'", 56'" of the distance element 34 lies in a plane other than that perpendicular to the long axis of the distance element 34'".

According to FIG. 3 the connecting element 20 of the compression or distraction rod 32 is angled or bent in one direction as a result of the particular arrangement of the distance elements 34', 34" and 34'" with respect to one another and their special form at the ends 54', 56', 54", 56" and 54'", 56'". Furthermore, by rotating the individual distance elements 34', 34" and 34'" with respect to one another the compressive or distractive action and the bracing force can be precisely adjusted.

The embodiment of the apparatus 10 in accordance with the invention for the stiffening and/or correction of part of the vertebral column shown in FIG. 4 likewise differs from that according to FIG. 1 basically with respect to the special arrangement and form of the distance elements 34, 34' and 34'". All the components that correspond to those of the embodiment of the apparatus 10 according to FIG. 1 are again indicated by the same reference numerals.

In the apparatus 10 according to FIG. 4 there is provided, in addition to the connecting element 20 that connects two screw-shaped retaining devices 12 to one another, an additional rod-shaped connecting element 60 that can be received by retaining devices 12. The connecting element 60 can, as illustrated in FIG. 4, be arranged at least partly and substantially in parallel with the connecting element 20 and be fixed relative to the latter. For this purpose there is non-detachably disposed at the at least one distance element 34"", substantially in parallel therewith, an additional distance element 34. According to FIG. 4 the distance element 34"" and the distance element 34 are joined to one another, for example, by a welded joint 62.

Figure 2A:
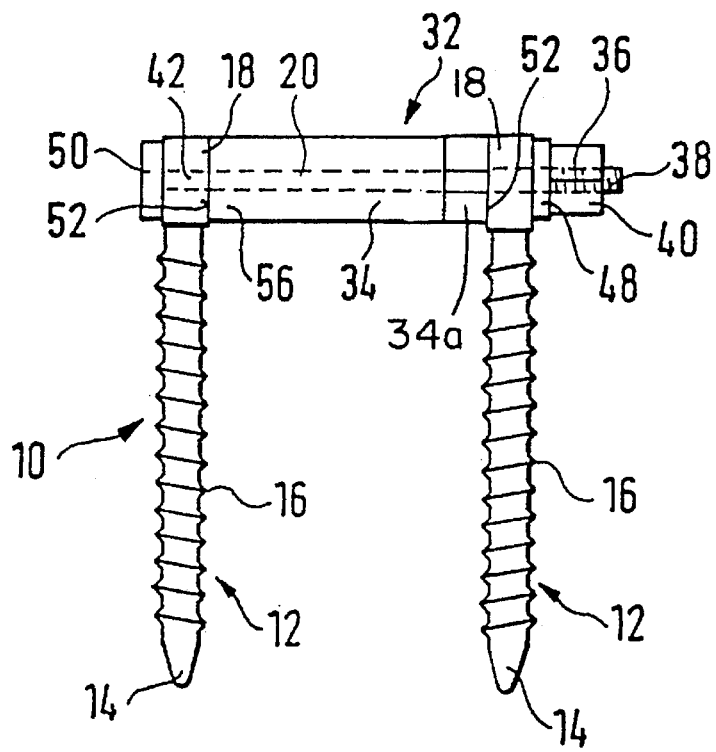
Figure 5:
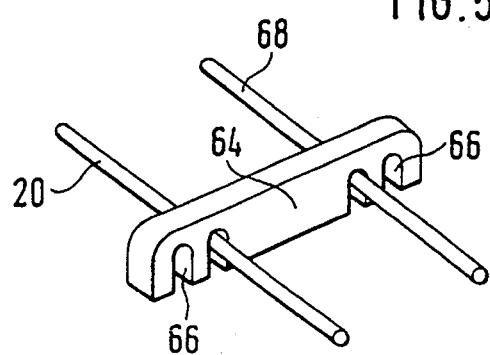
FIG. 5 shows a retaining device in accordance with the invention.

In alternative and/or cumulative elaboration of the invention, two rod-shaped connecting elements 20, 68 receivable by the retaining devices 12 can, as indicated schematically in FIG. 5, be connected to one another by way of holding elements 64. The holding elements 64 are provided with two or more slotlike or similar recesses 66, which serve to receive the two rod-shaped connecting elements 20, 60 substantially without play. According to FIGS. 1 to 4, the distance elements 34, 34', 34", 34'" and 34"" can all be made of various lengths, making it possible to employ the apparatus 10 flexibly. Thus, as shown in FIG. 2a, is an illustration of the structure as shown in FIGS. 1 and 2, with an element 34 and a second element 34a of a different length than element 34. FIG. 2a clearly illustrates the adjacent distance elements 34 and 34a to control the spacings between the detaining devices 12.

In addition, the faces 52, 52', 52", 52'" and 52"" of each distance element 34, 34', 34", 34'" and 34"" are roughened to provide rotation-stabilized contact with the retaining device(s) 12 and/or the neighboring distance element(s) 34, 34', 34", 34'" and 34"". FIG. 4a illustrates a particular roughened surface on one end of a distance element 34. In particular, the faces 52, 52', 52", 52'", 52"" of each distance element 34, 34', 34", 34'" and 34"" are provided with grooves, notches or the like and projections etc., illustrated in FIG. 4a of the drawings, which are disposed approximately radially with respect to the long axis of the distance elements 34, 34', 34", 34'" and 34"".

The retaining devices 12 and/or the rod-shaped connecting element 20, 60, 68 and/or the nuts 40, 46 that cooperate with the rod-shaped connecting element 20, 60, 68 are preferably made of metal, in particular titanium or an alloy thereof. The same applies to the distance element(s) 34, 34', 34", 34'" and 34"", which alternatively can also consist of a somewhat elastic/flexible material, in particular polyethylene.

The present invention is not restricted to the exemplary embodiments described above. In particular, it is conceivable that instead of screw-shaped retaining devices 12, hook-shaped retaining devices (not illustrated) could be employed, which can be attached to the individual vertebrae of the affected part of the vertebral column in a conventional manner.

All the characteristics disclosed in the application documents are claimed as essential to the invention, to the extent that they are new to the state of the art singly or in combination.

I claim:

1. An apparatus for attachment to a vertebrae column having at least two vertebral comprising first and second screw-shaped retaining devices (12), each said device being adapted to be fixed to one vertebrae of the vertebral column and are attached to a rod (32) which connects the retaining devices (12) to one another, the improvement wherein said rod (32) includes an elongated rod-shaped connecting element (20) having a first end and a second end, said first and second screw-shaped retaining devices (12) being mounted on said connecting element and movable along the connecting element, at least one distance element (34, 34', 34'', 34''', 34'''') movably mounted on the rod-shaped connecting element (2) between said first and second retaining devices (12) and establishing and maintaining a selected distance between said first and second retaining devices (12), said connecting element having a screw thread (38) on said first end of said connecting element and having an abutment element (44) on said second end of said connecting element and a fixing member threaded onto said screw thread with the retaining devices and said at least one distance element between the fixing member and the abutment element, the fixing member for moving said first retaining device, so that said at least one distance element extends from the first retaining device to the second retaining device to be in abutment with both the first and the second retaining device, while said fixing member abuts the first retaining device and said abutment member abuts the second retaining device to fix said retaining devices (12) and said at least one distance element (34, 34', 34'', 34''', 34'''') on said connecting element.

2. The apparatus according to claim 1, wherein said at least one distance element (34) has a long axis and having a first and a second end (54, 56), said first and second ends each having a planar end face (52) which lies in a plane perpendicular to the long axis of the distance element (34).

3. The apparatus according to claim 1, wherein said at least one distance element has a long axis and opposite end faces and at least one of the opposite end faces (52') lies in a plane offset by an angle from a plane perpendicular to the long axis of the distance element (34').

4. The apparatus of claim 1, wherein said at last one distance element includes a plurality of distance elements (34, 34', 34'', 34''', 34''''), each one of said plurality of distance elements having a fixed length and having a different length from the other of said distance elements of said plurality of distance elements.

5. The apparatus of claim 4, wherein each of said distance elements (34, 34', ÷'', 34''', 34'''') has a first and second end face, each of said first and second end faces is roughened to provide rotationally stabilized contact with said retaining device (12) and said adjacent distance element (34, 34', 34'', 34''', 34'''').

6. The apparatus of claim 4, wherein each of said distance elements includes substantially located radially oriented grooves and projections to provide rotationally stabilized contact with the retaining devices (12) and between adjacent distance elements (34, 34', 34'', 34''', 34'''').

7. The apparatus according to claim 1, wherein said at least one distance element (34''') has an outer surface, a key surface on said outer surface, said key surface adapting said at least one distance element (34''') for receiving a matching tool for rotating of said at least one distance element on said connecting element.

8. The apparatus of claim 1, wherein said rod shaped connector element is a first rod shaped connector element, said apparatus further including a second rod-shaped connecting element (60, 68) located at least partly and substantially in parallel with said first rod-shaped connecting element (20), at least one second distance element on said second connecting element, and a mount unit mounting said second rod-shaped connecting element in position relative to the first connecting element (20).

9. The apparatus of claim 8, wherein one of said at least one second distance elements is nondetachably attached to said second connecting element (60) in substantially parallel relation to said at least one distance element (34) on said first connecting element (20).

10. The apparatus of claim 8, including holding elements (64) connected to said first and said second rod-shaped connecting elements (20, 68) and supporting said connecting elements to one another.

11. The apparatus of claim 10, wherein each of said holding elements (64) includes at least two recesses (66) to receive the first and second rod-shaped connecting elements (20, 68) and said recesses being substantially the same shape as said connecting elements to support the connecting elements with minimal play.

12. The apparatus according to claim 1, wherein each of said screw-shaped retaining devices (12) comprises a screw shaft (14) with a screw thread (16) to be screwed into a vertebrae and a screw head (18) fixed in position on the rod-shaped connecting element (20).

13. The apparatus according to claim 12, wherein said screw head includes a bore (22) for mounting on said rod-shaped connecting element (20) said bore having a shape substantially the same as said connecting element to minimize play therebetween.

14. The apparatus according to claim 12, wherein said screw head (18) includes a longitudinal slot to receive the rod-shaped connecting element (20), said slot having a shape substantially the same as said connecting element to minimize play therebetween.

15. The apparatus according to claim 12, wherein the screw head (18) is offset from said screw shaft (14) of the screw-shaped retaining device (12), said head having an outwardly extending longitudinal bridge extending parallel to the screw shaft and a cross bridge connected to the longitudinal bridge and to said screw shaft, said cross bridge extending laterally from said longitudinal bridge to said screw shaft.

16. The apparatus of claim 1, wherein said fixing member is a nut and said abutment element is a nut, and at least one of said retaining devices (12), said rod-shaped connecting element (20, 60, 68) and said nuts (40, 46) are made of a metal alloy.

17. The apparatus of claim 1, wherein said at least one distance element (34, 34', 34'', 34''', 34'''') is made of titanium.

18. The apparatus of claim 1 wherein said at least one distance element (34, 34', 34'', 34''', 34'''') is made of an elastic material.

19. The apparatus of claim 18 wherein said elastic material is polyethylene.

20. The apparatus of claim 1 wherein said at least one distance element is made of titanium alloy.

\* \* \* \* \*